United States Patent
Takahashi et al.

(10) Patent No.: US 7,247,020 B2
(45) Date of Patent: Jul. 24, 2007

(54) DRILL SET FOR DENTAL SCREW IMPLANT FIXTURE WITH SELF-TAP

(75) Inventors: Masashi Takahashi, Tokyo (JP); Yataro Komiyama, Tokyo (JP); Takao Okada, Ibaraki (JP); Norio Kojima, Tokyo (JP)

(73) Assignee: GC Corporation, Tokyo (JP)

( * ) Notice: Subject to any disclaimer, the term of this patent is extended or adjusted under 35 U.S.C. 154(b) by 469 days.

(21) Appl. No.: 10/653,591

(22) Filed: Sep. 3, 2003

(65) Prior Publication Data

US 2004/0063067 A1    Apr. 1, 2004

(30) Foreign Application Priority Data

Sep. 26, 2002    (JP) .............................. 2002-281398

(51) Int. Cl.
*A61C 3/02*    (2006.01)
(52) U.S. Cl. ...................................... 433/165
(58) Field of Classification Search ................. 433/165, 433/174, 173
See application file for complete search history.

(56) References Cited

U.S. PATENT DOCUMENTS

| | | | |
|---|---|---|---|
| 4,185,383 A | * | 1/1980 | Heimke et al. ............. 433/173 |
| 5,000,686 A | | 3/1991 | Lazzara et al. |
| 5,259,398 A | * | 11/1993 | Vrespa ....................... 128/898 |
| 5,741,267 A | * | 4/1998 | Jorneus et al. ............. 606/102 |

FOREIGN PATENT DOCUMENTS

| | | |
|---|---|---|
| DE | 200 13 654 | 1/2001 |
| DE | 102 04 324 | 8/2002 |
| EP | 0 424 734 | 5/1991 |
| EP | 0 819 410 | 1/1998 |
| EP | 0 997 112 | 5/2000 |
| JP | 07-080002 | 3/1995 |
| JP | 10-211218 | 8/1998 |
| JP | 2001-512348 | 8/2001 |

OTHER PUBLICATIONS

Patent Abstracts of Japan, JP 2001-321392, Nov. 20, 2001.

* cited by examiner

*Primary Examiner*—Melba Bumgarner
(74) *Attorney, Agent, or Firm*—Oblon, Spivak, McClelland, Maier & Neustadt, P.C.

(57) ABSTRACT

A drill set for adjusting an implant hole for a self-tap dental screw implant fixture comprises with a diameter $d_2$ at the point of a cutting blade equivalent to a diameter $D_3$ of the tip end of the fixture, a diameter $d_1$ at the back end of the blade equivalent to the maximum root diameter of a first male screw $1e$ or smaller, and a length $l_1$ of the blade larger than the entire length $L_1$ of the fixture 1, and the second drill 3 with a diameter $d_5$ at the point of a tapered tip end cutting blade $3b$ equivalent to the diameter $D_3$, and a diameter $d_3$ at the back end of a tapered back end cutting blade $3a$ equivalent to the maximum root diameter of the first male screw $1e$ and smaller than the maximum crest diameter thereof, both the blades $3a$, $3b$ forming two-step taper shape.

2 Claims, 3 Drawing Sheets

DRILL SET FOR DENTAL SCREW IMPLANT FIXTURE WITH SELF-TAP

BACKGROUND OF THE INVENTION

1. Field of the Invention

The present invention relates to a drill set for a dental screw implant fixture with a self-tap. When treating a lost tooth part to recover lost function, the drill set is used for forming and finally adjusting an implant hole in a jawbone at the lost tooth location. A dental screw implant fixture having a self-tapping function at a tip end thereof is implanted where the tooth was lost.

2. Description of the Conventional Art

To treat lost teeth, a technique using a bridge and a technique using a denture has been generally practiced.

However, in the technique using a bridge, healthy natural teeth on both sides of the lost tooth are cut to form piers, and a dental prosthesis positioned at the lost tooth area is fixed between metallic members engaged and fixed on the piers. Therefore, not only healthy natural teeth must be cut for providing the piers, but also the process has a disadvantage in that an occlusion pressure is not directly applied to the inside of the oral cavity at the dental prosthesis positioned at the lost tooth area. Thus, bone resorption occurs in that area.

In the technique using a denture, a dental prosthesis is used that is formed by fixing an artificial tooth on a denture plate formed with a synthetic resin or the like. In this technique, because occlusion pressure is applied to the dental prosthesis bore by remaining natural teeth and/or the oral mucosa adjacent to the denture, there are some cases where uncomfortable feeling is caused during use. Accordingly, gustatory acceptors scattered in the tissue of the oral mucosa are covered with the denture plate to blunt gustation. Another disadvantage is that resorption of an alveolar ridge occurs upon using a prolonged period.

As a result of finding that metallic titanium is favorably bonded to bone, the following dental implant technique has been developed and practiced as a therapy for solving the problems. That is, as employing the "osseointegration", a dental implant fixture formed with metallic titanium to be a pier of a dental prosthesis is implanted in an implant hole formed at the lost tooth location to exert the function of a dental root of a natural tooth. A dental prosthesis is connected and fixed on the oral cavity side of the dental implant fixture.

In the remedy using the dental implant, because a dental prosthesis can be fixed without covering the oral mucosa, a natural tooth feel can be obtained without occurrence of unfavorable feeling and blunting of gustation upon wearing the dental prosthesis. Furthermore, an advantage is also obtained in that an appropriate occlusion force is applied to the jawbone, so as to suppress to a minimum level the bone resorption which might occur assuming that no dental implant fixture is implanted. Therefore, remedies using a dental implant are being rapidly developed and are being applied to loss of a sole tooth, local loss of two or more teeth, and an anodont jawbone (whole teeth loss).

The part of the dental implant fixture, which is implanted in the implant hole formed in the jawbone at the lost tooth location assuming the osseointegration, used in the dental implant remedy is generally formed into such a shape that is substantially equivalent to a tooth root. The surface shape thereof is, for example, a cylindrical shape (disclosed, for example, in FIGS. 1 and 3 of JP-A-7-80002) and a screw shape formed by providing a male screw on a cylindrical part of a body of a straight dental implant fixture (disclosed, for example, in FIG. 1 of JP-A-10-211218). Upon implanting the cylindrical dental implant fixture into a jawbone, an implant hole having a diameter equivalent to or slightly smaller than the diameter of the cylindrical part of the body of the cylindrical dental implant fixture is formed in the jawbone. The cylindrical dental implant fixture is pressed into the implant hole by hitting. However, there are disadvantages in that it is difficult to ensure stable fixation upon implanting due to difficulty in forming an accurate implant hole and difficulty in adjustment of an allowance for press fitness corresponding to the property of the bone. Additionally, a large burden is applied to a patient.

On the other hand, upon implanting the screw dental implant fixture in a jawbone, an implant hole having a diameter that is substantially equivalent to a root diameter of the male screw provided on the dental implant fixture is provided in the jawbone, and in general, a female screw capable of being screwed with the male screw provided on the screw dental implant fixture is provided on the implant hole with a tap. This is followed by screwing the screw dental implant fixture thereinto. Accordingly, there are some cases, depending on property of the bone, where difficulty occurs upon providing such a female thread on the implant hole that enables stable fixation upon implanting. Therefore, a prolonged period of time is required to form the female screw in the implant hole. This can apply a large burden to a patient.

In order to solve the problems, several screw dental implant fixtures have been proposed (for example, in FIGS. 1 and 2 of JP-A-2001-321392, and JP-A-2001-512348) in which a self-tapping function is previously provided to the dental implant fixture, whereby it can be implanted while forming a female thread in the implant hole formed in the jawbone at the lost tooth part. The screw dental implant fixture with a self-tap has improved fixation after implanting, and simpler in operation owing to the formation of the female thread attained simultaneously with the implantation. Further, in order to provide, a space for housing cut chips of the jawbone upon cutting the female thread, and to improve the fixation by providing a taper shape similar to a tooth root on the tip end part of the male screw implanted in the implant hole. Such a dental implant fixture is being widely used that has a taper shape on the tip end of the male screw and has on the tip end a cutting blade and a concave part provided continuously with the cutting blade.

As a result, the stability of the dental implant fixture immediately after implanting into the implant hole formed in the jawbone at the lost tooth location (initial fixing property) is improved. Thus, such a remedy receives attention in that an occlusion pressure can be applied to the dental implant fixture immediately after the implantation of the dental implant fixture in the implant hole formed in the jawbone or in an earlier stage after the implantation.

However, a drill for forming and finally adjusting the implant hole in the jawbone at the lost tooth part for screw dental implant fixture with a self-tap has a chevron tip end and a cutting blade formed continuously thereto capable of forming a circular hole having a diameter that is substantially equivalent to the maximum root diameter of the screw dental implant fixture with a self-tap. Therefore, in the case where the implant hole is formed by using the drill to such a depth that is substantially equivalent to the length, with which the screw dental implant fixture with a self-tap is implanted, the taper part at the tip end of the screw dental implant fixture with a self-tap is not in contact with the jawbone. Thus the tip may be less stable upon fixation. In the case where, on the other hand, the implant hole is provided to such a length that corresponds to the starting point of the taper part at the tip end of the screw dental implant fixture with a self-tap, there are such disadvantages in that the cut amount of the jawbone with the cutting blade provided on the taper part at the tip end of the screw dental implant fixture with a self-tap is increased. Therefore, the cut chips of the jawbone cannot be housed in the concave part provided continuously with the cutting blade. Also, it fails to ensure the stability upon fixation by applying a suitable load to the ostein of the jawbone.

SUMMARY OF THE INVENTION

An object of the present invention is to solve the problems associated with the conventional art and to provide a drill set for a dental screw implant fixture with a self-tap that can form such an implant hole in a jawbone at a lost tooth part that can provide stable initial fixing by favorably contacting the screw dental implant fixture with a self-tap with the jawbone over the entire implant hole upon implanting the screw dental implant fixture with a self-tap by screwing into the implant hole provided in the jawbone at the lost tooth part.

As a result of earnest investigations made by the inventors to solve the above-noted problems, it has been found that the object of the invention can be attained by using a set of two drills rather than using only one drill for adjusting the final shape of the implant hole as in the conventional art. i.e., a first drill is used having a diameter corresponding to the point of the taper part at the tip end of the screw dental implant fixture with a self-tap. A second drill is used next for cutting a part corresponding to the body part of the screw dental implant fixture with a self-tap and to a part from the starting point to a midstream point before the point of the taper part thereof.

The invention relates to a drill set for a dental screw implant fixture with a self-tap containing a first drill and a second drill.

The first drill is a taper drill having a diameter at the point of a cutting blade being substantially equivalent to a diameter of the tip end of the screw dental implant fixture with a self-tap; having a diameter at the back end of the cutting blade being equivalent to or smaller than a maximum root diameter of a first male screw provided on the oral cavity side of the screw dental implant fixture with a self-tap; and having a length of the cutting blade being larger than an entire length of the screw dental implant fixture with a self-tap.

The second drill is a two-step taper drill having a diameter of the point of a cutting blade substantially equivalent to the diameter of the tip end of the screw dental implant fixture with a self-tap. The diameter of the back end of the cutting blade is substantially equivalent to the maximum root diameter of the first male screw provided on the oral cavity side of the screw dental implant fixture with a self-tap and is smaller than a maximum crest diameter thereof. The second drill has a tapered back end cutting blade having a taper substantially equivalent to a taper of the first male screw of the screw dental implant fixture with a self-tap, on a part from the back end of the cutting blade in a length of from $\frac{1}{5}$ to a substantially equivalent length of a length of the first male screw of the screw dental implant fixture with a self tap. The second drill has a tapered tip end cutting blade on a part from the front end of the back end cutting blade to a tip end position having a diameter substantially equivalent to the diameter of the tip end of the screw dental implant fixture with a self-tap.

It is preferred that markings indicating a standard cutting depth are provided on the first drill and the second drill, respectively.

BRIEF DESCRIPTION OF THE DRAWINGS

FIGS. 2A and 2B are elevation views showing an example of the drill set for a dental screw implant fixture with a self-tap according to the present invention, in which FIG. 2A shows a first drill, and FIG. 2B shows a second drill.

DESCRIPTION OF THE PREFERRED EMBODIMENTS

A drill set for a dental screw implant fixture with a self-tap according to the present invention will be described below with reference to the figures.

Figure 1:
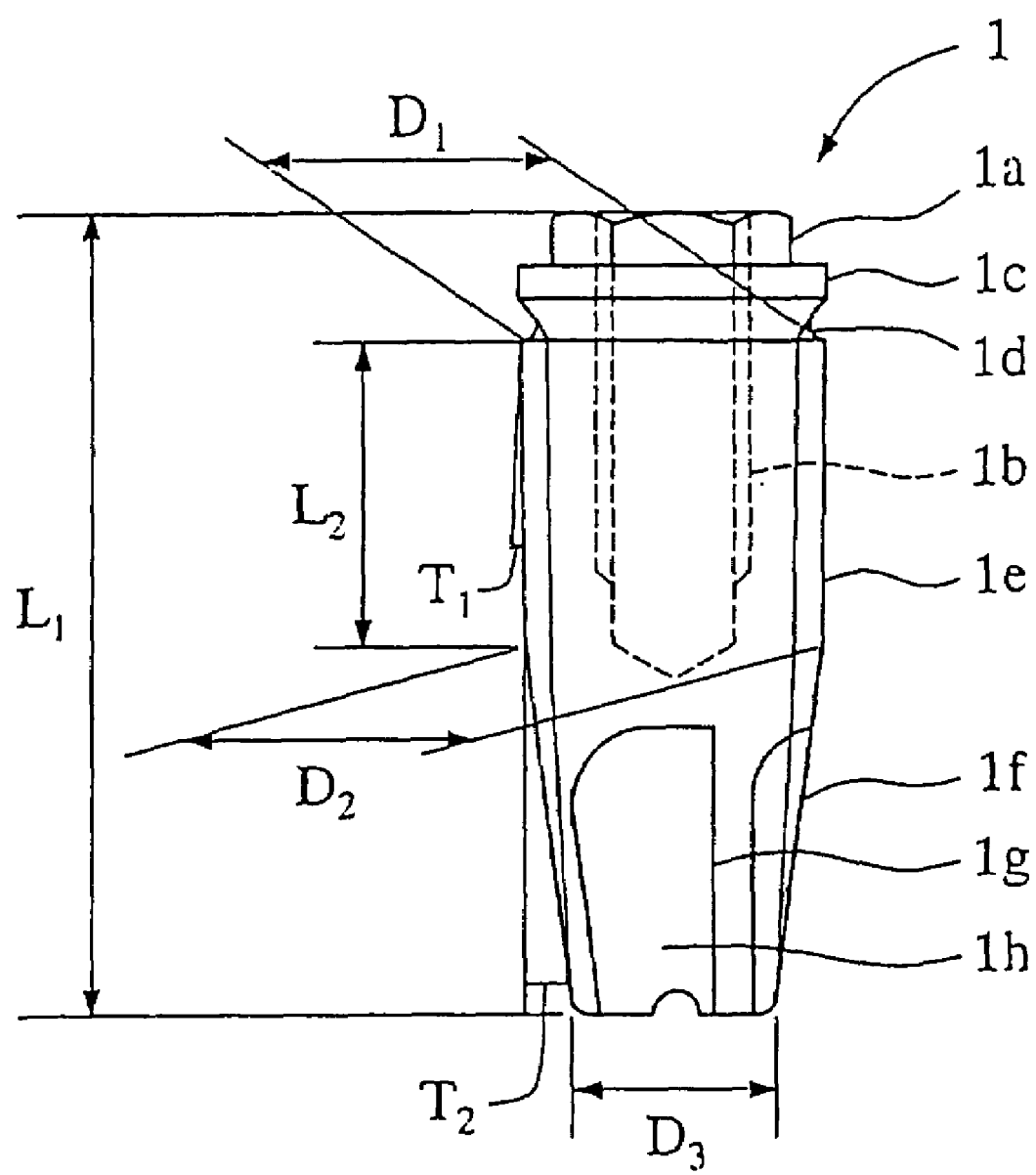
FIG. 1 is an elevation view showing an example of a screw dental implant fixture with a self-tap to be implanted in an implant hole provided in a jawbone at a lost tooth part, the shape of which is adjusted by using the drill set for a dental screw implant fixture with a self-tap according to the present invention.
Figure 2:
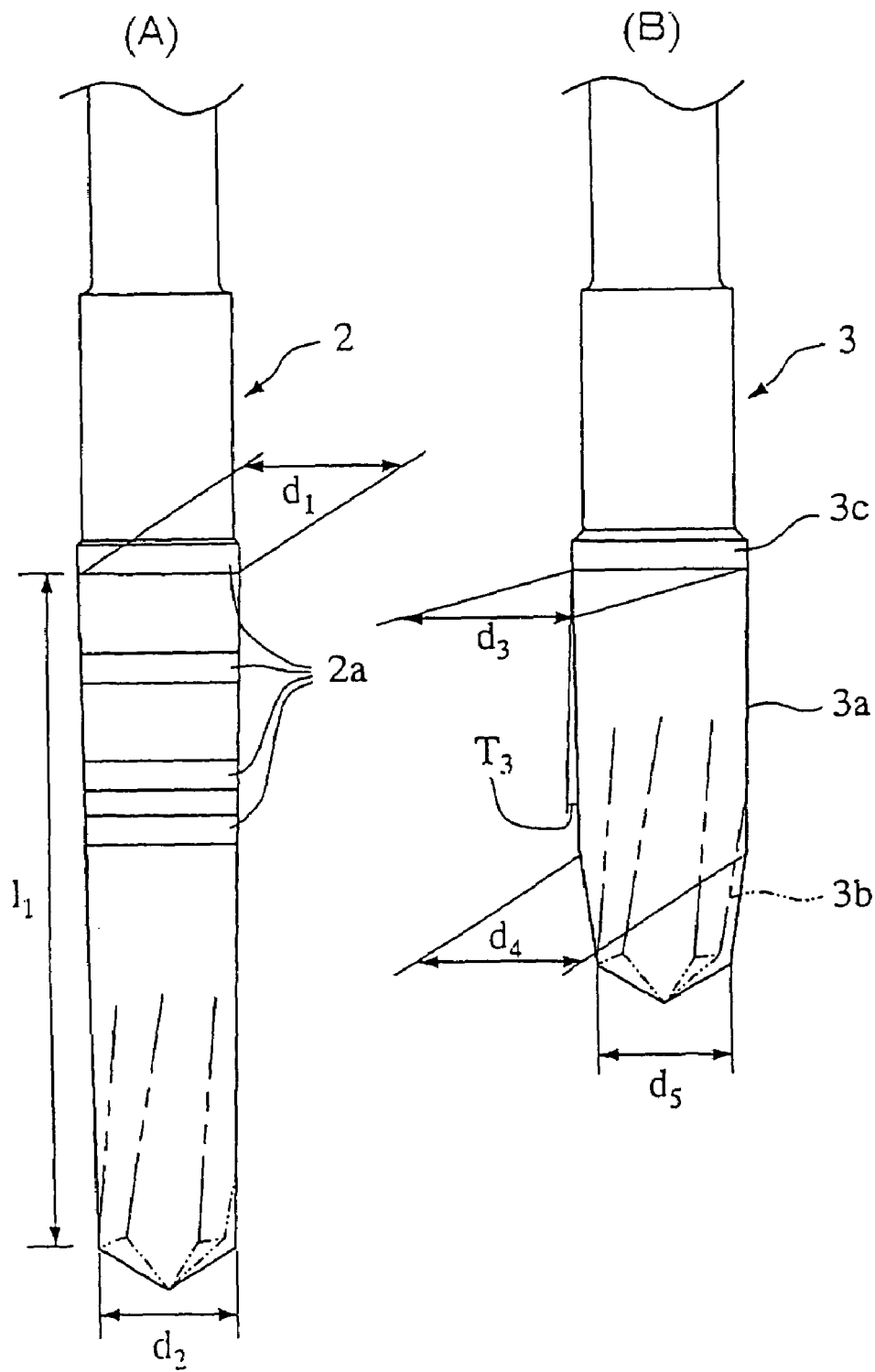
Figure 3:
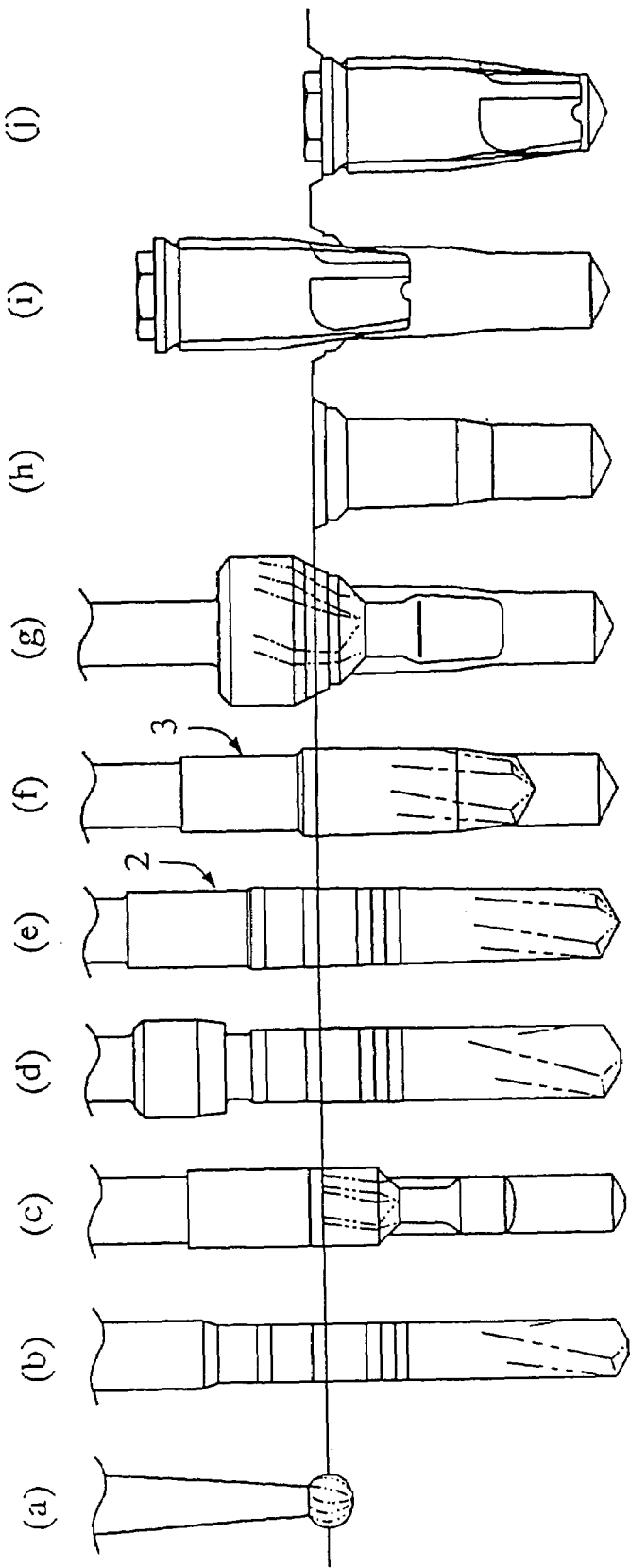
FIG. 3 is a cross sectional view showing an example of a process for implanting a screw dental implant fixture with a self-tap by providing an implant hole in a jaw bone at a lost tooth part.

FIG. 1 is an elevation view showing an example of a screw dental implant fixture with a self-tap to be implanted in an implant hole provided in a jawbone at a lost tooth location. The shape of the hole is adjusted by using the drill set for a dental screw implant fixture with a self-tap according to the present invention. FIGS. 2A and 2B are elevation views showing an example of the drill set for a dental screw implant fixture with a self-tap according to the present invention. FIG. 2A shows a first drill, and FIG. 2B shows a second drill. FIG. 3 is a cross sectional view showing an example of a process for implanting a screw dental implant fixture with a self-tap by providing an implant hole in a jaw bone at a lost tooth part.

In the figures, the numeral 1 denotes a dental screw implant fixture with a self-tap having a shape shown in FIG. 1. The implant has an entire length $L_1$ formed with metallic titanium, which has bioinertness and strength and is capable of favorably connecting to bone, in which a convex part 1a having a polygonal columnar shape (a hexagonal columnar shape in the example shown in the figure) is provided for preventing relative rotation with a dental prosthesis (not shown in the figure). The prosthesis is to be connected and fixed on the end surface on the oral cavity side, and a female thread 1b, in which a screw (not shown in the figure) for connecting and fixing the dental prosthesis is to be screwed, is provided in the axial direction through the center of the polygonal columnar convex part 1a. On an outer circumference continued from the polygonal columnar convex part 1a, a cylindrical collar 1c, a notch 1d, a first male thread 1e having a taper $T_1$ with smaller dwindling and a length $L_2$, and a second male screw 1f having a taper $T_2$ with larger dwindling than the taper $T_1$ of the first male screw 1e and the same pitch as the first male screw 1e are provided in this order from the end on the oral cavity side, and on the second male screw 1f, a cutting blade 1g for assisting the self-tapping function and a concave part 1h formed continuously with the cutting blade 1g are provided from the lower end toward the oral cavity side.

The cylindrical collar 1c is firstly provided on the outer circumference on the oral cavity side to obtain such an effect that the collar 1c prevents bacteria from invading into the implant hole. The notch 1d is provided continuous with the cylindrical collar 1c, whereby upon being implanting the dental screw implant fixture with a self-tap 1 into the implant hole formed in the jawbone at the lost tooth part, the notch 1d functions as a stopper by making the surface of the notch 1d on the oral cavity side in contact with the jawbone. In order to obtain these functions, it is preferred that the diameter of the cylindrical collar 1c is larger than the maximum crest diameter D, of the first male screw 1e.

The male screw (thread), which is formed on the part to be implanted in the implant hole formed in the jawbone at the lost tooth part by screwing, is provided continuous with the notch 1d is constituted with the first male screw 1e and the second male screw 1f. The first male screw 1e has the taper $T_1$ with smaller dwindling, in which the crest diameter $D_1$ at the end on the oral cavity side is larger than the crest diameter $D_2$ on the tip end. The second male screw 1f has the taper $T_2$ with larger dwindling than the taper $T_1$ of the first male screw 1e, a diameter $D_3$ at the tip end thereof, and the same pitch as the first male screw 1e. This is because, in the case where the male screw provided on the outer circumference of the dental screw implant fixture with a self-tap has a taper shape, not only the entire male screw implanted in the jawbone is maintained to be surely in contact therewith through the implanting period and the functional period of implanting the dental implant fixture with a self-tap 1 in the implant hole formed in the jawbone at the lost tooth part, so as to improve the stability against an external force, but also the initial fixing property is improved. However, in the case where the male screw has a constant taper shape over the entire length thereof, the taper cannot have large dwindling. Thus, there are such dangerous possibilities that it is in contact with a tooth root of the adjacent tooth or another dental implant fixture with a self-tap adjacently implanted, and the dental screw implant fixture with a self-tap 1 thus implanted is exposed from the surface of the bone. In order to avoid such dangerous possibilities, therefore, the male screw is constituted with the first male screw 1e with a smaller dwindling and the second male screw 1f with a larger dwindling. The first male screw 1e and the second male screw 1f must have the same pitch so as to prevent the second male screw 1f from impairing screwing of the first male screw 1e into the jawbone.

On the second male screw 1f, the cutting blade 1g for assisting the self-tapping function and the concave part 1h formed continuously with the cutting blade 1g are provided from the lower end toward the oral cavity side. According to the configuration, the formation of a female screw in the implant hole formed in the jawbone at the lost tooth part and the implantation of the dental screw implant fixture with a self-tap can be simultaneously carried out with accuracy without looseness to improve the fixing property after implanting. Further the operation time can be shortened, whereby the operation is simplified, and the burden applied to a patient is lightened.

The crest diameter of the male screw of the cutting blade 1g for assisting the self-tapping function at the end on the oral cavity side is preferably larger than the maximum root diameter of the first male screw 1e. This is because, in the case where the crest diameter of the male screw of the cutting blade 1g for assisting the self-tapping function at the end on the oral cavity side is smaller than the maximum root diameter of the first male screw 1e, upon implanting the first male screw 1e into the implant hole formed in the jawbone at the lost tooth part, it is necessary to tap a female screw with the first male screw 1e itself over the entire length on the jawbone, with which the first male screw 1e is in contact. This may apply a too large load to the first male screw 1e, and as a result, such a female screw is not formed in contact with the jawbone over the entire surface of the first male screw 1e. When the crest diameter of the male screw of the cutting blade 1g for assisting the self-tapping function at the end on the side of the oral cavity is smaller than the maximum crest diameter $D_1$ of the first male screw 1e and larger than the maximum root diameter of the first male screw 1e, the formation of a female screw corresponding to the first male screw 1e is incompletely but nearly completely finished in the part provided with the cutting blade 1g. Thus, the first male screw 1e is implanted with compression stress gradually applied in the radial direction. According to the configuration, the first male screw 1e receives larger compression stress in a part nearer to the oral cavity side, so as to attain firm fixation. Such allowance for receiving compression stress may not be necessarily large to obtain fixation, but a too large allowance thereof causes such dangerous possibilities of increase in implanting resistance, breakage of bone, and ambustion of surrounding bone due to occurrence of frictional heat. Therefore, it is preferred that the crest diameter of the male screw of the cutting blade 1g at the end on the oral cavity side is larger than the maximum root diameter of the first male screw 1e, whereby it is implanted in the state where the incomplete female screw is present.

The numeral 2 denotes a first drill shown in FIG. 2A constituting one part of the drill set for a dental screw implant fixture with a self-tap according to the present invention. The first drill 2 is formed in a taper shape and has a diameter $d_2$ at a point of a cutting blade being substantially equivalent to a diameter $D_3$ of the tip end of the screw dental implant fixture with a self-tap 1. The drill 2 has a diameter $d_1$ at the back end of the cutting blade being equivalent to or smaller than the maximum root diameter of the first male screw 1e provided on the oral cavity side of the screw dental implant fixture with a self-tap, and a length $l_1$ of the cutting blade being larger than an entire length $L_1$ of the screw dental implant fixture with a self-tap. It is preferred that a marked part 2a indicating a standard cutting depth is provided on the first drill 2.

The numeral 3 denotes a second drill shown in FIG. 2B constituting another part of the drill set for a dental screw implant fixture with a self-tap according to the present invention. The second drill 3 has a diameter $d_5$ of the point of a cutting blade substantially equivalent to the diameter $D_3$ of the tip end of the screw dental implant fixture with a self-tap 1. The second drill 3 has a diameter $d_3$ of the back end of the cutting blade substantially equivalent to the maximum root diameter of the first male screw 1e provided on the oral cavity side of the screw dental implant fixture with a self-tap 1. The diameter $d_3$ of the back end of the cutting blade is smaller than the maximum crest diameter thereof. The second drill 3 has a tapered backend cutting blade 3a having a taper $T_3$ substantially equivalent to the taper $T_1$ of the first male screw 1e of the screw dental implant fixture with a self-tap 1, on a part from the back end of the cutting blade in a length of from ⅕ to a substantially equivalent length of the length $L_2$ of the first male screw 1e of the screw dental implant fixture with a self tap 1. The second drill 3 has a tapered tip end cutting blade 3b on a part from the front end of the back end cutting blade 3a having a diameter $d_4$ to a tip end position having a diameter $d_5$ substantially equivalent to the diameter $D_3$ of the tip end of the screw dental implant fixture with a self-tap 1, so as to form a two-step taper shape. It is also preferred that a marked part 3c indicating a standard cutting depth is provided on the second drill 3.

The operation will be described below with reference to FIG. 3 for providing an implant hole in a jawbone at a lost tooth location by finally using the drill set for a dental screw implant fixture with a self-tap according to the present invention containing the first drill 2 and the second drill 3, and then implanting the dental screw implant fixture with a self-tap 1 therein.

Firstly, a small datum hole is provided with a positioning drill at a position of a lost tooth on the oral cavity side, on which the dental screw implant fixture with a self-tap 1 is to be implanted (step a). A hole having a length slightly larger than the entire length L, of the dental screw implant fixture with a self-tap 1 is provided in the jawbone at that position with a drill having a diameter smaller than the diameter $D_3$ at the tip end of the dental screw implant fixture with a self-tap 1 (step b). A shallow hole having a diameter substantially equivalent to the diameter $d_2$ at the point of a cutting blade of the first drill 2 is then provided on the oral cavity side with a drill having a guide at a tip end thereof with a diameter substantially equivalent to the diameter of the hole having been provided in the step b (step c). Thereafter, a hole having a depth substantially equivalent to the depth of the hole having been provided in the step b with a drill having a diameter substantially equivalent to the diameter $d_2$ at a point of a cutting blade of the first drill 2 (step d).

Subsequently, the shape of the hole having been provided is adjusted to a taper shape by drilling with the first drill 2 to a depth substantially equivalent to the depth of the hole having been provided (step e). Thereafter, the hole is drilled with the second drill 3 to such a depth that the back end of the back end cutting blade 3a reaches the end of the hole on the oral cavity side, so as to form a hole having the following shape. That is, the hole has a diameter on the oral cavity side that is substantially equivalent to the maximum root diameter of the first male screw 1e provided on the screw dental implant fixture with a self-tap 1 on the oral cavity side and is smaller than the maximum crest diameter thereof, and has a taper shape with the taper $T_3$ dwindling toward the bottom of the hole. However the hole thus provided does not reach the bottom of the hole having been provided with the first drill 2 (step f).

Thereafter, the end of the hole thus formed on the oral cavity side is expanded with a drill to correspond to the notch 1d and the cylindrical collar 1c of the dental screw implant fixture with a self-tap 1 (step g). Then the drill is withdrawn from the hole to complete the operation for providing the hole (step h). The dental screw implant fixture with a self-tap 1 is screwed in the hole thus provided (step i). The dental screw implant fixture with a self-tap 1 is then completely implanted into the implant hole with assistance from the cutting blade 1g for assisting the self-tapping function and the concave part 1h formed continuously with the cutting blade 1g provided from the lower end toward the side oral cavity on the second male screw 1f of the dental screw implant fixture with a self-tap 1 (step j).

In the foregoing operation, an implant hole is provided in the jawbone at the lost tooth part by finally using the drill set for a dental screw implant fixture with a self-tap according to the present invention. The part on the oral cavity side of the implant hole, on which the first male screw 1e of the dental screw implant fixture with a self-tap is screwed, is formed to have such a configuration that is to be tapped to a substantially uniform thickness with the first male screw 1e of the dental screw implant fixture 1. Therefore, a substantially uniform screwed state is obtained between the jawbone around the implant hole and the first male screw 1e of the dental screw implant fixture with a self-tap 1, and such a part is not formed that the jawbone and the first male screw 1e of the dental screw implant fixture with a self-tap 1 are not in contact with each other.

The part on the deep part of the implant hole, on which the second male screw 1f of the dental screw implant fixture with a self-tap 1 is screwed, is provided with a female screw by tapping the jawbone with the cutting blade 1g for assisting the self-tapping function and the concave part 1h formed continuously with the cutting blade 1g provided on the second male screw 1f of the dental screw implant fixture 1 from the lower end toward the oral cavity side. Therefore, such a part is not produced that the jawbone and the second male screw 1f of the dental screw implant fixture with a self-tap 1 are not in contact with each other. Further, cut chips of the jawbone produced upon tapping are surely housed in the concave part 1h formed continuously with the cutting blade 1g provided on the second male screw 1f of the dental screw implant fixture 1 from the lower end toward the oral cavity side, so as to avoid a possibility of applying a burden to the jawbone having not been cut on the deep part of the implant hole.

As described in the foregoing, the drill set for a dental screw implant fixture with a self-tap according to the present invention is characterized by containing a first drill and a second drill.

The first drill is a taper drill having a diameter at the point of a cutting blade substantially equivalent to a diameter of the tip end of the screw dental implant fixture with a self-tap. The first drill has a diameter at the back end of the cutting blade equivalent to or smaller than a maximum root diameter of a first male screw provided on the oral cavity side of the screw dental implant fixture with a self-tap. The length of the cutting blade is larger than an entire length of the screw dental implant fixture with a self-tap.

The second drill is a two-step taper drill having a diameter of the point of a cutting blade substantially equivalent to the diameter of the tip end of the screw dental implant fixture with a self-tap. The second drill has a diameter of the back end of the cutting blade substantially equivalent to the maximum root diameter of the first male screw provided on the oral cavity side of the screw dental implant fixture with a self-tap and smaller than a maximum crest diameter thereof. The second drill has a tapered back end cutting blade having a taper substantially equivalent to a taper of the first male screw of the screw dental implant fixture with a self-tap, on a part from the back end of the cutting blade in a length of from ⅕ to a substantially equivalent length of a length of the first male screw of the screw dental implant fixture with a self tap; and having a tapered tip end cutting blade on a part from the front end of the back end cutting blade to a tip end position having a diameter substantially equivalent to the diameter of the tip end of the screw dental implant fixture with a self-tap.

According to the cutting operation with the second drill, the part on the oral cavity side of the implant hole, on which the first male screw of the dental screw implant fixture with a self-tap is screwed, is formed to have such a configuration that is to be tapped to a substantially uniform thickness with the first male screw of the dental screw implant fixture 1. Therefore, a substantially uniform screwed state is obtained between the jawbone around the implant hole and the first male screw of the dental screw implant fixture with a self-tap. Such a part is not formed that the jawbone and the first male screw of the dental screw implant fixture with a self-tap are not in contact with each other. Furthermore, because the cutting operation with the second drill is carried out in addition to the cutting operation with the first drill, the part on the deep part of the implant hole, on which the second male screw of the dental screw implant fixture with a self-tap is screwed, is provided with a female screw (thread) by tapping the jawbone with the cutting blade for assisting the self-tapping function and the concave part formed continuously with the cutting blade provided on the second male screw of the dental screw implant fixture from the lower end toward the oral cavity side. Therefore, such a part is not formed that the jawbone and the second male screw of the dental screw implant fixture with a self-tap are not in contact with each other, and cut chips of the jawbone formed upon tapping are surely housed in the concave part formed continuously with the cutting blade provided on the second male screw of the dental screw implant fixture from the lower end toward the oral cavity side so as to avoid a possibility of applying a burden to the jawbone having not been cut on the deep part of the implant hole.

Furthermore, such a part is not formed that the dental screw implant fixture with a self-tap and the jawbone around the implant hole are not in contact with each other, which has occurred in the conventional case where the shape of the implant hole is finally adjusted with only one straight drill. Thus, the load applied to the jawbone by the first male screw and the second male screw provided on the dental screw implant fixture with a self-tap is substantially uniform, whereby osseointegration can be established in an earlier stage.

Moreover, stable fixation of the dental screw implant fixture with a self-tap in the jawbone at the lost tooth part can be obtained by implanting with screwing the dental screw implant fixture with a self-tap in the implant hole formed in the jawbone at the lost tooth location. Therefore, such a remedy can be carried out in that an occlusion pressure can be applied to the dental implant fixture immediately after the implantation of the dental implant fixture in the implant hole formed in the jawbone or earlier after the implantation.

The drill set for a dental screw implant fixture with a self-tap according to the present invention thus exerts various effects as having been described, and therefore, it provides significant values by contributing to the field of dentistry.

What is claimed is:

1. A drill set for a dental screw implant fixture with a self-tap comprising:

a first drill including, a diameter at a point of a cutting blade substantially equivalent to a diameter of a tip of a bottom end of a screw dental implant fixture;

a diameter at a back end of the cutting blade equivalent to or smaller than a maximum root diameter of a first male screw provided on an oral cavity side of the screw dental implant fixture;

a length of the cutting blade being larger than an entire length of the screw dental implant fixture; and a second drill being a two-step taper drill including a diameter of a point of a cutting blade substantially equivalent to the diameter of a tip end of the screw dental implant fixture;

a diameter of a back end of a tapered back end cutting blade substantially equivalent to the maximum root diameter of the first male screw provided on the oral cavity side of the screw dental implant fixture and smaller than a maximum crest diameter thereof;

the tapered back end cutting blade having a taper substantially equivalent to a taper of the first male screw of the screw dental implant fixture from the back end of the cutting tapered back end blade in a length of from $\frac{1}{5}$ to a substantially equivalent length of a length of the first male screw of the screw dental implant fixture; and a tapered tip end cutting blade adjacent to the tapered back end cutting blade and adjacent to a tip, the tapered tip end cutting blade being less parallel to an axis of rotation of the second drill than is the tapered back end cutting blade from a front end of the back end cutting blade to a tip end position having a diameter substantially equivalent to the diameter of the tip of the bottom end of the screw dental implant fixture.

2. A drill set for a dental screw implant fixture with a self-tap as claimed in claim 1, wherein marked parts indicating a cutting depth are provided on each of the first drill and the second drill.

* * * * *